United States Patent
Ryan

(10) Patent No.: US 9,055,952 B2
(45) Date of Patent: Jun. 16, 2015

(54) IRRIGATION CATHETER

(75) Inventor: Garrett Ryan, Surry Hills (AU)

(73) Assignee: CATHRX LTD, Homebush Bay (AU)

( * ) Notice: Subject to any disclaimer, the term of this patent is extended or adjusted under 35 U.S.C. 154(b) by 116 days.

(21) Appl. No.: 13/816,727

(22) PCT Filed: Aug. 12, 2011

(86) PCT No.: PCT/AU2011/001018
§ 371 (c)(1),
(2), (4) Date: Feb. 12, 2013

(87) PCT Pub. No.: WO2012/019229
PCT Pub. Date: Feb. 16, 2012

(65) Prior Publication Data
US 2013/0144288 A1    Jun. 6, 2013

Related U.S. Application Data

(60) Provisional application No. 61/373,725, filed on Aug. 13, 2010.

(51) Int. Cl.
*A61N 1/00*    (2006.01)
*A61B 18/14*    (2006.01)
*A61B 18/00*    (2006.01)

(52) U.S. Cl.
CPC ... *A61B 18/1492* (2013.01); *A61B 2018/00577* (2013.01); *A61B 2018/1467* (2013.01); *A61B 2218/002* (2013.01)

(58) Field of Classification Search
CPC ............. A61B 2018/00577; A61B 2018/1467; A61B 18/1492; A61B 2218/002
USPC ....................................................... 606/20–44
See application file for complete search history.

(56) References Cited

U.S. PATENT DOCUMENTS

| 5,913,856 A | 6/1999 | Chia et al. |
| 2002/0002329 A1 | 1/2002 | Avitall |
| 2008/0249522 A1 | 10/2008 | Pappone et al. |

FOREIGN PATENT DOCUMENTS

| WO | 2010011820 A2 | 1/2010 |
| WO | 2010063078 A1 | 6/2010 |

OTHER PUBLICATIONS

Search Report for International Application No. PCT/AU2011/001018, mailed Dec. 6, 2011, 4 pages.
Written Opinion for International Application No. PCT/AU2011/001018, mailed Dec. 6, 2011, 4 pages.
International Preliminary Report on Patentability, for International Application No. PCT/AU2011/001018, dated Feb. 19, 2013, 5 pages.

*Primary Examiner* — Scott Getzow
(74) *Attorney, Agent, or Firm* — TraskBritt

(57) ABSTRACT

An irrigation catheter includes a handle, a catheter sheath with at least one ablation electrode proximal the distal end of the catheter sheath and a stylet for deflecting the distal end of the catheter sheath. The ablation electrode includes at least one irrigation opening in it. The irrigation catheter further includes a fluid-carrying formation formed on the catheter sheath under the ablation electrode. The fluid-carrying formation is in fluid communication with the irrigation lumen of the catheter sheath so that fluid is conveyed from the irrigation lumen to the irrigation opening.

20 Claims, 4 Drawing Sheets

IRRIGATION CATHETER

CROSS-REFERENCE TO RELATED APPLICATIONS

This application is a national phase entry under 35 U.S.C. §371 of International Patent Application PCT/AU2011/001018, filed Aug. 12, 2011, designating the United States of America and published in English as International Patent Publication WO 2012/019229 A1 on Feb. 16, 2012, which claims the benefit under Article 8 of the Patent Cooperation Treaty and under 35 U.S.C. §119(e) to U.S. Provisional Patent Application Ser. No. 61/373,725, filed Aug. 13, 2010, the disclosure of each of which is hereby incorporated herein by this reference in its entirety.

TECHNICAL FIELD

This disclosure relates, generally, to a catheter and, more particularly, to an irrigation catheter.

BACKGROUND

Any discussion of the prior art throughout the specification should in no way be considered as an admission that such prior art is widely known or forms part of common general knowledge in the field.

In the conduction of Maze-type procedures, an ablation catheter is used to ablate heart tissue to attempt to clear heart arrhythmias. Generally, a dot ablation is made and this is repeated by re-positioning a tip, ablation electrode of an ablation catheter. This is an extremely time-consuming process. The temperature of the tip electrode also needs to be carefully maintained to ensure that it does not result in excessive ablation of the tissue occurring.

If a clinician could form longer lesions, fewer manipulations would be required. This would reduce the time to conduct the procedure, which would be beneficial for all concerned. A difficulty with forming longer lesions is maintaining the temperature of any longer electrode during the ablation procedure.

BRIEF SUMMARY

It is an object of the present invention to overcome or ameliorate at least one of the disadvantages of the prior art, or to provide a useful alternative.

In an aspect, there is provided an irrigation catheter that includes:
- a tubular member of a non-conductive material having a proximal end and a distal end, the tubular member being a multi-lumen member having a plurality of lumens extending from the proximal end to the distal end of the tubular member, one of the lumens being an irrigation lumen;
- at least one ablation electrode arranged on the tubular member proximally of the distal end of the tubular member, the at least one electrode having at least one irrigation opening defined in it; and
- a fluid-carrying formation arranged in the tubular member beneath the at least one electrode, the fluid-carrying formation being in fluid flow communication with the irrigation lumen of the tubular member for conveying fluid from the irrigation lumen to the at least one irrigation opening of the at least one electrode.

The catheter may include an end ablation electrode carried at the distal end of the tubular member, and the at least one ablation electrode may be at least one further electrode arranged proximally of the end electrode. The end electrode may have at least one irrigation opening defined in it in communication with the irrigation lumen of the tubular member. The catheter may include a plurality of further ablation electrodes arranged at longitudinally spaced intervals along the tubular member, each further ablation electrode having at least one irrigation opening defined in it and each further ablation electrode having a fluid-carrying formation associated with it.

Each fluid-carrying formation may be in the form of a recessed formation defined in a wall of the tubular member. It will be appreciated that each recessed formation, which may be in the form of an annular groove, is formed to such a depth in the wall of the tubular member that it intersects the irrigation lumen so that the irrigation lumen opens into a floor of each recessed formation.

Each electrode may be mounted over its recessed formation in a fluid-tight manner to inhibit escape of fluid past an edge of the electrode. Edges of the electrode may be sealed by using an adhesive at a junction with the tubular member to inhibit fluid leakage.

The irrigation openings in the electrodes are sized to cater for a differential in fluid pressure along the length of the tubular member. More particularly, the openings may increase in size toward the distal end of the tubular member.

Each electrode may carry a plurality of openings at circumferentially spaced intervals about the electrode.

The catheter may include a connector arranged at a proximal region of the tubular member for connection to a source of irrigation fluid, the connector being in fluid flow communication with the irrigation lumen of the tubular member by a fluid supply formation arranged in the wall of the tubular member beneath the connector.

The fluid supply formation may be a recessed formation defined in the wall of the tubular member to be in fluid flow communication with the irrigation lumen of the tubular member. The connector may be mounted over the recessed formation in a fluid-tight manner to inhibit escape of fluid past an edge of the connector. Once again, edges of the connector may be sealed by using an adhesive at a junction with the tubular member to inhibit fluid leakage.

BRIEF DESCRIPTION OF THE DRAWINGS

Preferred embodiments of the invention will now be described, by way of example only, with reference to the accompanying drawings in which.

DETAILED DESCRIPTION

Figure 1:
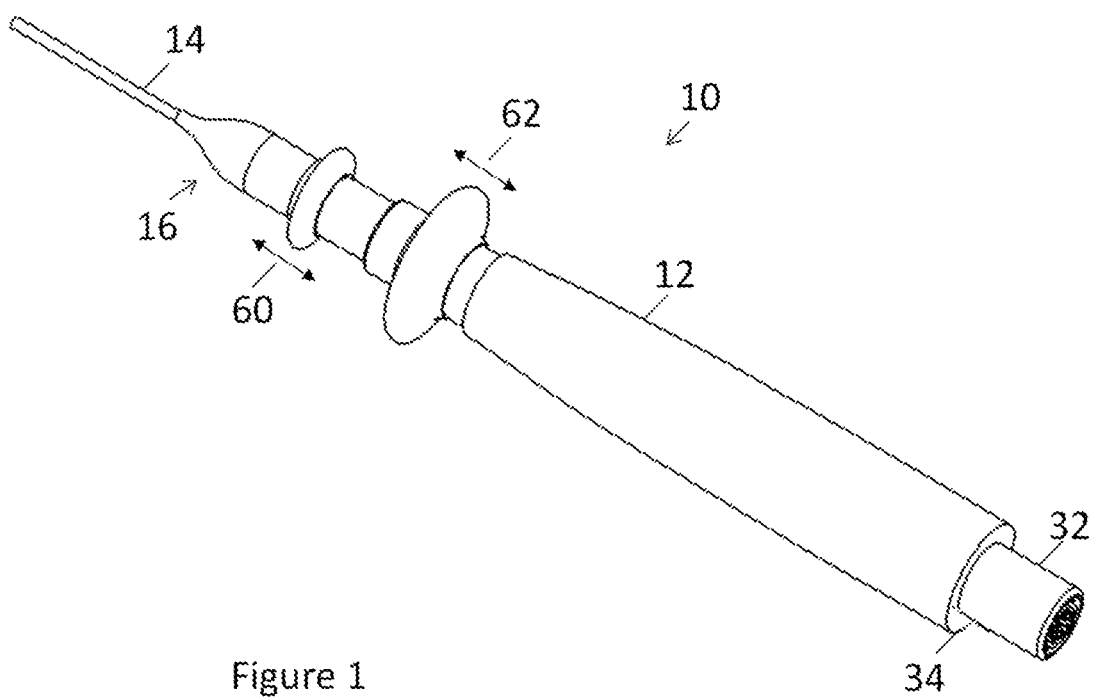
FIG. 1 shows a perspective view of a catheter assembly.
Figure 5:
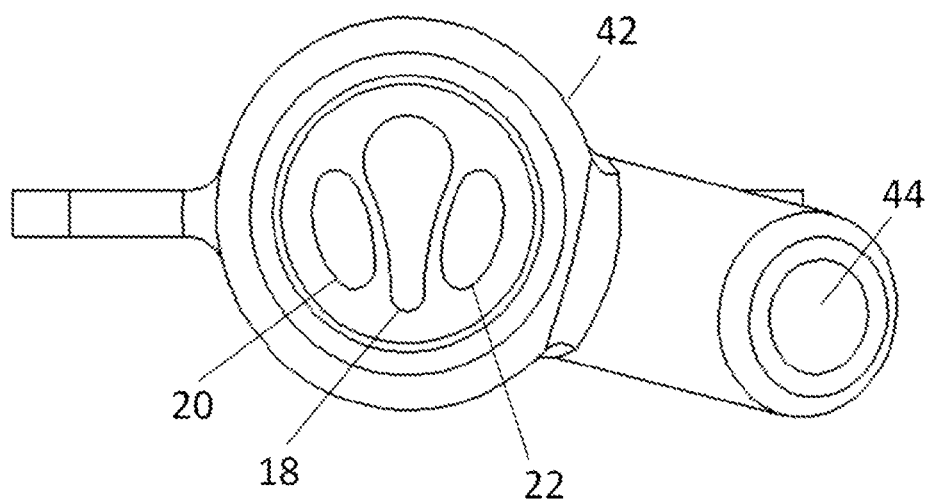
FIG. 5 shows a schematic, cross-sectional end view of the connector of FIG. 4.

In FIG. 1, reference numeral 10 generally designates an irrigation catheter. The catheter 10 includes a handle 12. A catheter sheath 14 extends from a distal end 16 of the handle 12. The catheter sheath 14 defines a plurality of lumens 18, 20 and 22 (FIG. 5). The lumen 18 is a deflection stylet lumen for receiving a deflection stylet 24. The catheter handle includes a control knob for controlling the deflection by moving the control knob in the direction of arrow 62. The catheter handle may also include a size selector control knob for controlling the size of deflection curvature by moving the size selector knob in the direction of arrow 60. The lumen 20 is a conductor lumen and has a plurality of conductors (not shown) received therein, the conductors extending from electrodes 28 (FIG. 2) carried on a distal part 30 of the catheter sheath 14. The conductors extend through the handle 12 to an electrical connector 32 (FIG. 1) arranged at a proximal end 34 of the handle 12.

Figure 4:
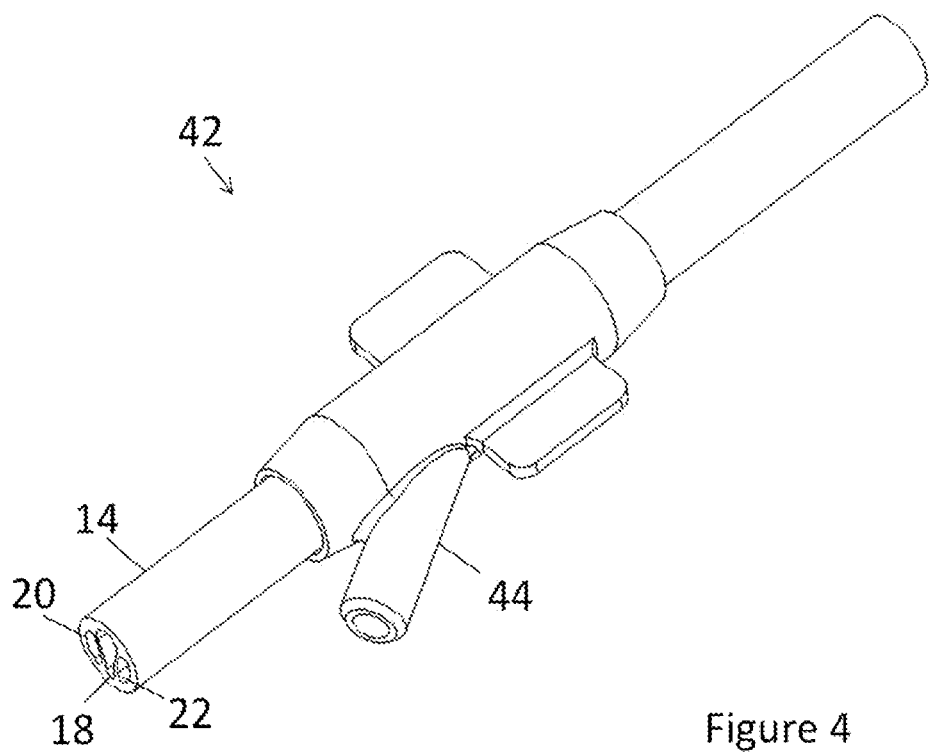
FIG. 4 shows a perspective view of a connector of the irrigation catheter.

The lumen 22 is an irrigation lumen for providing irrigating fluid to the electrodes 28 at the distal part 30 of the catheter sheath 14. The irrigation lumen 22 communicates with a female Luer connector 42 (FIG. 4) arranged at a proximal end of the catheter sheath 14 for connection to a supply of irrigation fluid (not shown).

The catheter 10 is, as indicated above, an irrigation catheter and includes the irrigation lumen 22. It is also to be noted that the electrodes 28 on the distal part 30 of the catheter sheath 14 are longer than they are wide and, when used for ablation, longer lesions can result. This is especially true if a bipolar type operation is effected where two, generally adjacent, electrodes 28 are energized simultaneously to cause RF energy flow between the adjacent electrodes 28.

Figure 2:
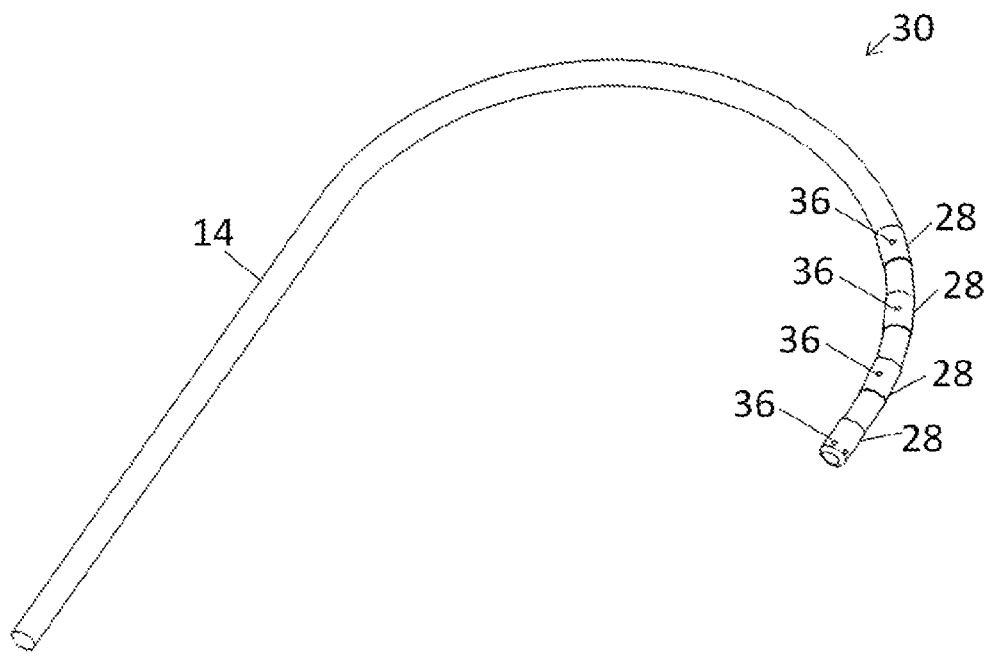
FIG. 2 shows a perspective view of a distal part of a catheter sheath of an embodiment of an irrigation catheter.
Figure 6:
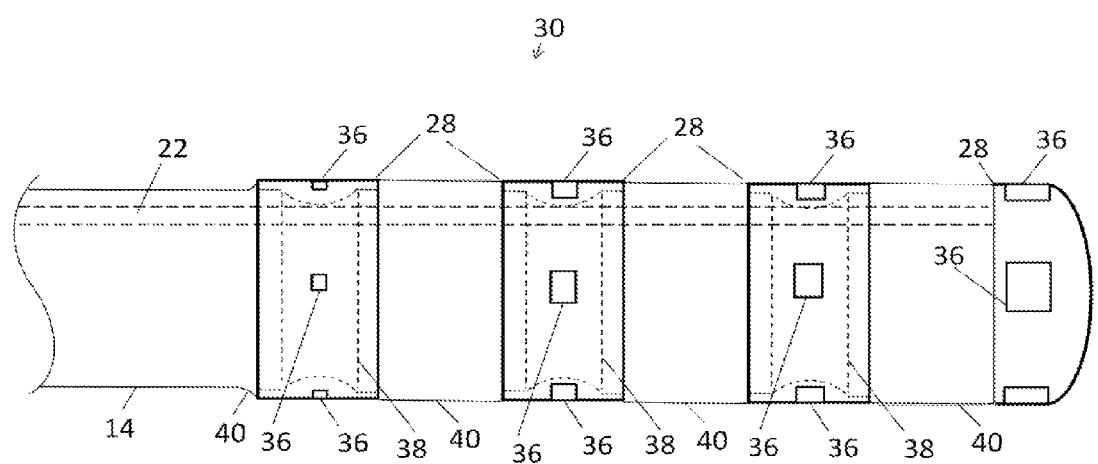
FIG. 6 shows a side view of the distal part of the irrigation catheter.

As illustrated in FIGS. 2 and 6, each electrode 28 has at least one, and, preferably, a plurality of irrigation openings 36 formed in the body of the electrode 28. The benefit of this arrangement is that the irrigation fluid is expelled on to the surface of the ablation electrode 28 and cools the surrounding region of the electrode 28. Preferably, as shown in FIG. 6, each electrode 28 has a plurality of such openings 36 arranged at circumferentially spaced intervals. Thus, for example, four such openings 36 may be provided in each electrode 28 spaced approximately 90° from each other.

To receive the irrigation fluid, which may be a saline solution, from the irrigation lumen 22, each of the ring electrodes 28 communicates with the irrigation conduit via a fluid-carrying formation 38 arranged beneath the ring electrode 28. This is not necessary with respect to the tip electrode 28, since the irrigation lumen 22 opens out into the interior of the tip electrode 28.

The fluid-carrying formation is in the form of an annular groove 38 defined in the material of the catheter sheath 14.

An adhesive (not shown) is applied about each side edge of each ring electrode 28 and the proximal edge of the tip electrode 28 to inhibit leakage of irrigation fluid from the groove through the edges of the electrodes 28. In addition, in the manufacture of the distal part 30 of the catheter sheath 14, the material from which the distal part 30 is made is heat treated by the application of a sacrificial heat-shrink sleeve (not shown). The heat treatment causes parts 40 of the catheter sheath 14 between the electrodes 28 and proximally of the proximal electrode 28 swell radially to form a sealing fillet about the side edges of the electrodes 28. This further serves to inhibit the escape of irrigation fluid past the edges of the electrodes 28.

To supply fluid to the distal part 30 of the catheter sheath 14 via the irrigation lumen, a female Luer connector 42 is mounted on the catheter sheath 14. The connector 42 has a port 44 to which a supply of the irrigation fluid (not shown) is connectable for use.

Figure 3:
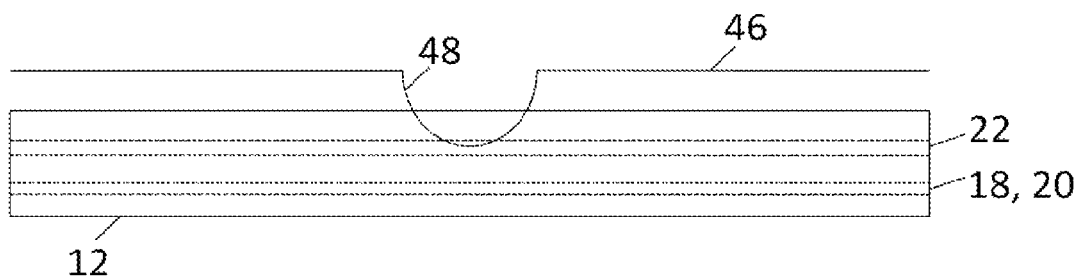
FIG. 3 shows a schematic, cross-sectional side view of a step in the manufacture of the irrigation catheter.

During the manufacture of the catheter sheath, to attach the connector 42 to the catheter sheath 14, a skive template 46 (FIG. 3) is mounted on the catheter sheath 14. The skive template 46 has a recessed region 48 within which a cutting implement, such as a blade, is insertable to cut away a part of the material of the catheter sheath to form a recess, which locally exposes the irrigation lumen 22 as seen in FIG. 3. Once the recess has been formed in the proximal region of the catheter sheath 14, the connector 42 is slid over the proximal end of the catheter sheath so that the port 44 abuts the recess and the port 44 is in communication with the irrigation lumen 22 (FIG. 5).

Edges of the connector 42, particularly around the port 44, are sealed by use of an appropriate adhesive such as a UV adhesive to inhibit leakage of fluid from the ends of the connector 42. When the template 46 is applied to the catheter sheath 14, mandrels (not shown) are inserted into the remaining lumens 18 and 20 of the catheter sheath 14 to inhibit collapse of the lumens 18 and 20.

It is to be noted from FIG. 6 that the openings 36 in the electrodes are sized to cater for pressure differential along the length of the catheter sheath 14. In particular, the openings 36 are of different sizes to cater for different pressures. The larger openings 36 are arranged toward the downstream end to ensure that substantially the same amount of irrigation fluid flows out of each of the electrodes 28 during an ablation procedure.

It is an advantage of the described embodiment that an irrigation catheter 10 is provided that contains multiple ablation electrodes, each of which is able to be irrigated. Moreover, the irrigation openings are contained within the electrodes so as to facilitate improved temperature control of the electrodes 28 during the ablation procedure. By having multiple openings in each electrode, a greater dispersion of the irrigation fluid is able to be achieved, thereby further assisting in temperature control of those electrodes 28.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics in one or more embodiments may be combined in any suitable manner, as would be apparent to one of ordinarily skill in the art from this disclosure.

As used herein, unless otherwise specified, the use of ordinal adjectives "first," "second," "third," etc., to describe a common object, merely indicate that different instances of like objects are referred to, and are not intended to imply that the objects so described must be in a given sequence, either temporally, spatially, in ranking, or in any other manner.

In the claims below and the description herein, any one of the terms "comprising," "comprised of" or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including," "which includes" or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The claims defining the invention are as follows:

1. An irrigation catheter, comprising:
a tubular member comprising a non-conductive material having a proximal end and a distal end, the tubular member having a plurality of lumens extending from the proximal end to the distal end of the tubular member, one lumen of the plurality of lumens being an irrigation lumen;
at least one ablation electrode arranged on the tubular member proximally of the distal end of the tubular member, the at least one ablation electrode having at least one irrigation opening defined in the at least one ablation electrode; and
a fluid-carrying formation arranged in the tubular member, the fluid-carrying formation located between an inner surface of the at least one ablation electrode and an outer surface of the tubular member, the fluid-carrying formation being in fluid flow communication with the irrigation lumen of the tubular member for conveying fluid from the irrigation lumen to the at least one irrigation opening of the at least one ablation electrode; and
wherein the at least one ablation electrode is mounted on the tubular member in a fluid-tight manner and is configured to inhibit escape of fluid past an edge of the at least one ablation electrode.

2. The catheter of claim 1, further comprising an end ablation electrode carried at the distal end of the tubular member, and the at least one ablation electrode is at least one further electrode arranged proximally of the end ablation electrode.

3. The catheter of claim 2, wherein the end ablation electrode has at least one irrigation opening defined in it in communication with the irrigation lumen of the tubular member.

4. The catheter of claim 2, wherein the at least one ablation electrode comprises a plurality of ablation electrodes arranged at longitudinally spaced intervals along the tubular member, each ablation electrode of the plurality of ablation electrodes having at least one irrigation opening defined in the respective ablation electrode, and wherein each ablation electrode of the plurality of ablation electrodes has a fluid-carrying formation associated with the respective ablation electrode, each fluid-carrying formation located between outer surface of the tubular member and an inner surface of the associated ablation electrode.

5. The catheter of claim 4, wherein each fluid-carrying formation comprises a recessed formation defined in a wall of the tubular member.

6. The catheter of claim 5, wherein each ablation electrode of the plurality of ablation electrodes is mounted over an associated recessed formation in a fluid-tight manner to inhibit escape of fluid past an edge of the ablation electrode.

7. The catheter of claim 4, wherein the at least one irrigation opening in each ablation electrode of the plurality of ablation electrodes is sized to cater for a differential in fluid pressure along a length of the tubular member.

8. The catheter of claim 4, wherein each ablation electrode of the plurality of ablation electrodes carries a plurality of openings at circumferentially spaced intervals about the ablation electrode.

9. The catheter of claim 1, further comprising a connector arranged at a proximal region of the tubular member for connection to a source of irrigation fluid, the connector being in fluid flow communication with the irrigation lumen of the tubular member by a fluid supply formation arranged in the wall of the tubular member beneath the connector.

10. The catheter of claim 9, wherein the fluid supply formation is a recessed formation defined in the wall of the tubular member to be in fluid flow communication with the irrigation lumen of the tubular member.

11. The catheter of claim 10, wherein the connector is mounted over the recessed formation in a fluid-tight manner to inhibit escape of fluid past an edge of the connector.

12. A catheter, comprising:
a tubular member including a non-conductive material having a proximal end and a distal end, the tubular member defining a plurality of lumens extending therethrough from the proximal end to the distal end of the tubular member, one lumen of the plurality of lumens being an irrigation lumen, the tubular member having at least one recess in an outer surface of the tubular member proximate the distal end of the tubular member, the at least one recess in fluid communication with the irrigation lumen; and at least one ablation electrode disposed on the tubular member over the at least one recess, the at least one ablation electrode having at least one irrigation opening extending through the at least one ablation electrode to the at least one recess.

13. The catheter of claim 12, wherein the at least one ablation electrode comprises a plurality of ablation electrodes disposed along the tubular member, each ablation electrode of the plurality of ablation electrodes having at least one irrigation opening extending therethrough, and wherein the tubular member has a plurality of recesses in the outer surface of the tubular member, each ablation electrode of the plurality of ablation electrodes disposed over an associated recess of the plurality of recesses.

14. The catheter of claim 13, wherein each ablation electrode of the plurality of ablation electrodes is sealed in a fluid tight manner over the associated recess of the plurality of recesses, such that fluid flowing through the irrigation lumen and into the recesses of the plurality of recesses flows out from the recesses only through the at least one irrigation opening extending through each ablation electrode of the plurality of ablation electrodes.

15. The catheter of claim 13, wherein the at least one irrigation opening in one ablation electrode of the plurality of ablation electrodes has a size different from a size of the at least one irrigation opening in another ablation electrode of the plurality of ablation electrodes.

16. The catheter of claim 15, wherein the at least one irrigation opening in the one ablation electrode has a larger size than the at least one irrigation opening in the another ablation electrode.

17. The catheter of claim 16, wherein the one ablation electrode is located closer to the distal end of the tubular member than the another ablation electrode.

18. The catheter of claim 17, wherein the at least one irrigation opening in the one ablation electrode and the at least one irrigation opening in the another ablation electrode are sized and configured to provide a same amount of irrigation fluid flow out from the at least one irrigation opening in the one ablation electrode and the at least one irrigation opening in the another ablation electrode during an ablation procedure.

19. The catheter of claim 13, wherein each ablation electrode of the plurality of ablation electrodes has a plurality of openings extending therethrough, the openings of the plurality of openings arranged circumferentially about the ablation electrode.

20. The catheter of claim 12, further comprising a connector arranged at a proximal region of the tubular member for connection to a source of irrigation fluid, the connector being in fluid communication with the irrigation lumen of the tubular member.

* * * * *

UNITED STATES PATENT AND TRADEMARK OFFICE
CERTIFICATE OF CORRECTION

PATENT NO. : 9,055,952 B2  
APPLICATION NO. : 13/816727  
DATED : June 16, 2015  
INVENTOR(S) : Garrett Ryan Page 1 of 1

It is certified that error appears in the above-identified patent and that said Letters Patent is hereby corrected as shown below:

In the claims:
CLAIM 4,    COLUMN 6,    LINE 33,    change "between outer" to --between the outer--

Signed and Sealed this  
Fifteenth Day of March, 2016

Michelle K. Lee  
*Director of the United States Patent and Trademark Office*